United States Patent
Akiyoshi et al.

(10) Patent No.: US 11,045,437 B2
(45) Date of Patent: Jun. 29, 2021

(54) COMPOSITION FOR IMPROVING BRAIN FUNCTION

(71) Applicant: AJINOMOTO CO., INC., Tokyo (JP)

(72) Inventors: Shinobu Akiyoshi, Kawasaki (JP); Ami Ito, Kawasaki (JP); Tatsuya Hasegawa, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 16/550,733

(22) Filed: Aug. 26, 2019

(65) Prior Publication Data

US 2020/0061010 A1    Feb. 27, 2020

(30) Foreign Application Priority Data

Aug. 27, 2018 (JP) .............................. JP2018-158306

(51) Int. Cl.
| | |
|---|---|
| *A61K 31/197* | (2006.01) |
| *A61K 31/198* | (2006.01) |
| *A61K 31/405* | (2006.01) |
| *A61P 25/28* | (2006.01) |
| *A61K 31/401* | (2006.01) |

(52) U.S. Cl.
CPC .......... *A61K 31/198* (2013.01); *A61K 31/197* (2013.01); *A61K 31/401* (2013.01); *A61K 31/405* (2013.01); *A61P 25/28* (2018.01)

(58) Field of Classification Search
CPC .. A61K 31/197; A61K 31/198; A61K 31/405; A61P 25/28
See application file for complete search history.

(56) References Cited

U.S. PATENT DOCUMENTS

| | | |
|---|---|---|
| 2004/0248771 A1 | 12/2004 | Raggi |
| 2006/0128778 A1 | 6/2006 | Abe et al. |
| 2008/0114067 A1 | 5/2008 | Yamamoto |
| 2019/0247347 A1 | 8/2019 | Nishitani |

FOREIGN PATENT DOCUMENTS

| | | |
|---|---|---|
| GB | 2 381 451 A | 5/2003 |
| JP | 8-198748 A | 8/1996 |
| WO | WO 2004/028528 A1 | 4/2004 |
| WO | WO 2006/080086 A1 | 8/2006 |
| WO | WO 2007/145239 A1 | 12/2007 |
| WO | WO 2018/047980 A1 | 3/2018 |

*Primary Examiner* — Samira J Jean-Louis
(74) *Attorney, Agent, or Firm* — Oblon, McClelland, Maier & Neustadt, L.L.P.

(57) ABSTRACT

Compositions comprising (A) tyrosine, serine, alanine, aspartic acid and glutamic acid as active ingredients are useful for improving brain function and recovering from or suppressing fatigue and are highly safe and permit continuous ingestion or administration.

13 Claims, 7 Drawing Sheets
Specification includes a Sequence Listing.

Evaluation of cognitive function of mental stress model using Y-maze test

Measurement of blood GOT, GPT of mental stress model

Analysis of ATF3 expression in liver and thalamus in mental stress model

Analysis of hippocampus monoamine level in mental stress model

Evaluation of cognitive function of exercise fatigue model using NORT evaluation Analysis of ATF3 expression in liver, gastrocnemial muscle
and thalamus in exercise fatigue model Analysis of hepcidin (Hamp) expression in liver in exercise fatigue model

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
gaggattttg ctaacctgac acc                                           23

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ttgacggtaa ctgactccag c                                             21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gcctgagcag caccacctat                                               20

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
agcatttaca gcagaagatg caga                                          24
```

COMPOSITION FOR IMPROVING BRAIN FUNCTION

CROSS REFERENCES TO RELATED APPLICATIONS

This application claims priority to Japanese Patent Application No. 2018-158306, filed on Aug. 27, 2018, which is incorporated herein by reference in its entirety.

BACKGROUND OF THE INVENTION

Field of the Invention

The present invention relates to brain function improving compositions and fatigue recovery or suppressing compositions, each containing particular amino acids. The present invention also relates to methods for improving brain function and methods of recovering from or suppressing fatigue.

Discussion of the Background

An amino acid composition that suppresses an increase in the serotonin concentration in the brain due to exercise fatigue has been reported (see WO 2004/028528, which is incorporated herein by reference in its entirety). In addition, an amino acid composition that improves cognitive function in a senescence-accelerated mouse has been reported (see WO 2018/047980, which is incorporated herein by reference in its entirety). However, an amino acid composition effective for reducing brain dysfunction due to mental stress and exercise fatigue is not known.

SUMMARY OF THE INVENTION

Accordingly, it is one object of the present invention to provide amino acid compositions capable of improving disorders such as brain dysfunction and the like and suppressing fatigue, and permitting continuous ingestion or administration.

It is another object of the present invention to provide novel method of improving disorders such as brain dysfunction and the like and suppressing fatigue by administering such a composition.

These and other objects, which will become apparent during the following detailed description, have been achieved by the inventors' discovery that a combination of particular amino acids is effective for reducing brain dysfunction and fatigue caused by mental stress, physical stress and the like, and that the combination can reduce a decline in brain function such as cognitive function and the like and recover or suppress fatigue, which resulted in the completion of the present invention.

That is, the present invention provides the following.

(1) A composition for improving brain function comprising (A) tyrosine, serine, alanine, aspartic acid and glutamic acid as active ingredients.

(2) The composition of (1) further comprising (B) at least one kind selected from the group consisting of hydroxyproline, tryptophan and asparagine.

(3) The composition of (1) or (2) wherein the improvement of brain function is reduction of brain dysfunction caused by mental stress or exercise fatigue.

(4) The composition of (3) wherein the brain dysfunction is at least one kind selected from the group consisting of cognitive decline, chronic fatigue syndrome and depression.

(5) The composition of any of (1) to (4) wherein blending ratios in the composition are 0.5 to 1.5 parts by weight of serine, 0.5 to 1.5 parts by weight of alanine, 0.5 to 1.5 parts by weight of aspartic acid and 0.5 to 2.5 parts by weight of glutamic acid, per 1 part by weight of tyrosine.

(6) The composition of any of (2) to (5) wherein blending ratios in the composition are 0 to 2 parts by weight of hydroxyproline, 0 to 0.2 parts by weight of tryptophan and 0 to 2 parts by weight of asparagine, per 1 part by weight of tyrosine.

(7) The composition of any of (1) to (6) which is in a unit package form per serving comprising 6 mg to 180 g in total of (A) in the unit for single ingestion.

(8) The composition of any of (2) to (7) which is in a unit package form per serving comprising 6 mg to 180 g in total of (A) and (B) in the unit for single ingestion.

(9) A composition for fatigue recovery or fatigue suppression comprising (A) tyrosine, serine, alanine, aspartic acid and glutamic acid as active ingredients.

(10) The composition of (9) further comprising (B) at least one kind selected from the group consisting of hydroxyproline, tryptophan and asparagine.

(11) The composition of (9) or (10) wherein blending ratios in the composition are 0.5 to 1.5 parts by weight of serine, 0.5 to 1.5 parts by weight of alanine, 0.5 to 1.5 parts by weight of aspartic acid and 0.5 to 2.5 parts by weight of glutamic acid, per 1 part by weight of tyrosine.

(12) The composition of (11) wherein the blending ratios in the composition are 0 to 2 parts by weight of hydroxyproline, 0 to 0.2 parts by weight of tryptophan and 0 to 2 parts by weight of asparagine, per 1 part by weight of tyrosine.

(13) The composition of any of (9) to (12) which is in a unit package form per serving comprising 6 mg to 180 g in total of (A) in the unit for single ingestion.

(14) The composition of any of (10) to (12) which is in a unit package form per serving comprising 6 mg to 180 g in total of (A) and (B) in the unit for single ingestion.

(15) The composition of any of (1) to (14) which is a pharmaceutical product.

(16) The composition of any of (1) to (14) which is a food.

(17) A method for improving brain function, comprising administering an effective amount of a composition which comprises (A) tyrosine, serine, alanine, aspartic acid and glutamic acid as active ingredients to a subject in need thereof.

(18) The method according to (17) wherein said composition further comprises (B) at least one member selected from the group consisting of hydroxyproline, tryptophan and asparagine.

(19) The method according to (17), wherein said improvement of brain function is reduction of brain dysfunction caused by mental stress or exercise fatigue.

(20) The method according to (19), wherein said brain dysfunction is at least one kind selected from the group consisting of cognitive decline, chronic fatigue syndrome and depression.

(21) The method according to (17), wherein blending ratios in the composition are 0.5 to 1.5 parts by weight of serine, 0.5 to 1.5 parts by weight of alanine, 0.5 to 1.5 parts by weight of aspartic acid and 0.5 to 2.5 parts by weight of glutamic acid, per 1 part by weight of tyrosine.

(22) The method according to (18), wherein blending ratios in the composition are 0 to 2 parts by weight of hydroxyproline, 0 to 0.2 parts by weight of tryptophan and 0 to 2 parts by weight of asparagine, per 1 part by weight of tyrosine.

(23) The method according to (17), wherein said composition is in a unit package form per serving comprising 6 mg to 180 g in total of (A) in the unit for single ingestion.

(24) The method according to (18), wherein said composition is in a unit package form per serving comprising 6 mg to 180 g in total of (A) and (B) in the unit for single ingestion.

(25) A method for fatigue recovery or fatigue suppression, comprising administering an effective amount of a composition which comprises (A) tyrosine, serine, alanine, aspartic acid and glutamic acid as active ingredients to a subject in need thereof.

(26) The method according to (25), wherein said composition further comprises (B) at least one member selected from the group consisting of hydroxyproline, tryptophan and asparagine.

Effect of the Invention

According to the present invention, a composition capable of reducing a decline in brain function such as cognitive function and the like can be provided.

According to the present invention, a decrease in the intracerebral neurotransmitter level can be suppressed. Thus, a composition also effective for improving decreased motivation, depression symptom and the like can be provided.

According to the present invention, a composition capable of recovering and suppressing fatigue can be provided.

The active ingredient in the present invention is amino acid, and therefore, it can be easily ingested safely for a long term.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENT

Figure 1:
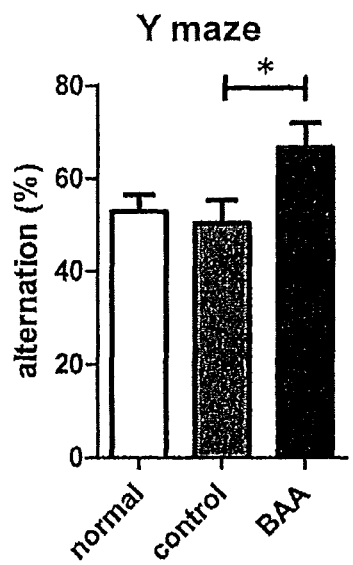
FIG. 1 is a graph showing an improving effect of a BAA composition on cognitive decline in a mental stress model. Normal: a group generally reared with oral administration of water. Control: a group reared in a cage with water with oral administration of water. BAA: a group reared in a cage with water with oral administration of amino acid composition BAA. $P<0.05$ in two groups connected by *.

The brain function improving composition of the present invention is a composition containing (A) tyrosine, serine, alanine, aspartic acid and glutamic acid as active ingredients (hereinafter sometimes to be generically referred to as the composition of the present invention).

In the present specification, the reduction of brain dysfunction or reduction of decline in brain function means to reduce or prevent a decrease in the brain function due to mental stress, exercise fatigue, infection, aging, obesity, disease and the like. Particularly, it means to prevent the brain function from becoming low due to mental stress and/or exercise fatigue, bring same to normal or prevent aggravation thereof.

The brain dysfunction includes cognitive decline, chronic fatigue syndrome, depression, chronic fatigue, troublesome feeling, decreased motivation, decline in concentration, memory decline, decline in judgment and the like. Among these, the composition of the present invention is preferably used for improvement of cognitive decline, decreased motivation, decline in concentration, memory decline, or decline in judgment.

The term "cognitive function" refers to high brain functions such as remembering, reasoning, calculating, understanding, suppressing, learning, thinking, communicating, problem solving ability and the like.

The cognitive decline that may be improved by the composition of the present invention includes cognitive decline due to dementia caused by various diseases and lesions such as Alzheimer's disease, frontotemporal lobar degeneration (Pick's disease etc.), Lewy body disease, cerebrovascular diseases and the like, cognitive decline due to aging, cognitive decline observed in healthy human, for example, decrease of abilities to remember, concentrate, think, be motivated, reason, solve problems and the like.

The use of the brain function improving composition of the present invention for the target such as human and the like may be therapeutic or non-therapeutic. As used herein, "non-therapeutic" is a concept that does not involve medical practice, namely, a concept that does not involve a method for surgery, treatment or diagnosis of human.

The fatigue recovery or suppressing composition of the present invention is a composition containing (A) tyrosine, serine, alanine, aspartic acid and glutamic acid as active ingredients (hereinafter sometimes to be generically referred to as the composition of the present invention).

The term "fatigue" means subjective fatigue such as boredom, discomfort, weakness and the like, objective fatigue such as quantitative or qualitative decline in work ability, and physiological fatigue which is a change in the physiological function that causes fatigue, when physical or mental work is continuously performed. Specific examples include mental fatigue, brain fatigue, physical fatigue, muscle fatigue and liver fatigue.

The fatigue also includes fatigue which is easily recovered by resting, overwork which is a state in which fatigue has accumulated, exhaustion or extreme fatigue which is a state in which strong fatigue prevents moving, and chronic fatigue which is fatigue over a long term.

The term "fatigue recovery" means to recover, improve, and accelerate recovery from fatigue, thereby achieving shift to a normal state. The term "fatigue suppression" means not only to reduce fatigue but also prevent fatigue.

The use of the fatigue recovery or suppressing composition of the present invention for a target such as human and the like may be therapeutic or non-therapeutic. As used herein, "non-therapeutic" is a concept that does not involve medical practice, namely, a concept that does not involve a method for surgery, treatment or diagnosis of human.

The composition of the present invention contains (A) tyrosine, serine, alanine, aspartic acid and glutamic acid (hereinafter sometimes to be respectively abbreviated as Tyr, Ser, Ala, Asp and Glu) as active ingredients. The composition of the present invention may further contain (B) at least one kind selected from the group consisting of hydroxyproline, tryptophan and asparagine (sometimes to be respectively abbreviated as Hypro, Trp and Asn), or a combination of 7 kinds in total including any two kinds from (B), or a combination of 8 kinds.

The amino acid to be contained in the composition of the present invention is not limited as long as the effect of the invention is not impaired; L-form or DL-form is preferable, and L-form is more preferable.

The amino acid in the present invention may be produced by any production method such as a protein hydrolysis method, a chemical synthesis method, an enzyme method, a fermentation method and the like, and commercially available products can also be used.

The amino acid in the present invention can also be obtained by enzymatically hydrolyzing a natural protein having the amino acid sequence.

The amino acid in the present invention can be used not only in a free form but also a salt form. The terms tyrosine, serine, alanine, aspartic acid, glutamic acid, hydroxyproline, tryptophan and asparagine in the present specification are each a concept also encompassing a salt. The salt form is not particularly limited as long as it is a pharmacologically acceptable salt, and an acid addition salt, salt with base and the like can be mentioned.

Concrete examples of the salt include salts with inorganic bases, salts with organic bases, salts with inorganic acids, salts with organic acids, salts with amino acid and the like.

Examples of the salts with inorganic bases include salts with alkali metals such as lithium, sodium, potassium and the like, salts with alkaline earth metals such as magnesium, calcium and the like, ammonium salt and the like.

Examples of the salts with organic bases include salts with an alkanolamine such as monoethanolamine, diethanolamine, triethanolamine and the like, salts with a heterocyclic amine such as morpholine, piperidine and the like, and the like.

Examples of the salts with inorganic acids include salts with a hydrohalic acid (hydrochloric acid, hydrobromic acid, hydroiodic acid etc.), sulfuric acid, nitric acid, phosphoric acid and the like.

Examples of the salts with organic acids include salts with a monocarboxylic acid such as formic acid, acetic acid, propanoic acid and the like; salts with a saturated dicarboxylic acid such as oxalic acid, malonic acid, malic acid, succinic acid and the like; salts with an unsaturated dicarboxylic acid such as maleic acid, fumaric acid and the like; salts with a tricarboxylic acid such as citric acid and the like; salts with a keto acid such as α-ketoglutaric acid and the like.

Examples of the salts with an amino acid include salts with an aliphatic amino acid such as glycine, alanine and the like; salts with an aromatic amino acid such as tyrosine and the like; salts with a basic amino acid such as arginine and the like; salts with an acidic amino acid such as aspartic acid, glutamic acid and the like; salts with an amino acid forming lactam such as pyroglutamic acid and the like; and the like.

The above-mentioned salts may each be a hydrate (hydrate salt), and examples of such hydrate include 1 hydrate to 6 hydrates and the like.

In the present invention, one kind of amino acid in a free form or the above-mentioned salt form may be used singly, or two or more kinds thereof may be used in combination.

In the present invention, tyrosine is preferably in a free form, serine is preferably in a free form, alanine is preferably in a free form, aspartic acid is preferably in a free form or a sodium salt or the like, glutamic acid is preferably in a free form or a sodium salt or the like, hydroxyproline is preferably in a free form, tryptophan is preferably in a free form, and asparagine is preferably in a free form, hydrate or the like.

In the composition of the present invention, the blending ratios of tyrosine, serine, alanine, aspartic acid and glutamic acid are generally (A-2) 0.5 to 1.5 parts by weight of serine, (A-3) 0.5 to 1.5 parts by weight of alanine, (A-4) 0.5 to 1.5 parts by weight of aspartic acid and (A-5) 0.5 to 2.5 parts by weight of glutamic acid, preferably, (A-2) 0.7 to 1.3 parts by weight, (A-3) 0.7 to 1.3 parts by weight, (A-4) 0.7 to 1.3 parts by weight, (A-5) 0.7 to 2.1 parts by weight, more preferably, (A-2) 0.9 to 1.1 parts by weight, (A-3) 0.9 to 1.1 parts by weight, (A-4) 0.9 to 1.1 parts by weight, (A-5) 0.9 to 2.1 parts by weight, each per 1 part by weight of (A-1) tyrosine when converted to L form and free form.

In the composition of the present invention, the blending ratios of tyrosine, serine, alanine, aspartic acid, glutamic acid, hydroxyproline, tryptophan and asparagine are generally (A-2) serine 0.5 to 1.5 parts by weight, (A-3) alanine 0.5 to 1.5 parts by weight, (A-4) aspartic acid 0.5 to 1.5 parts by weight, (A-5) glutamic acid 0.5 to 1.5 parts by weight, (B-1) hydroxyproline 0 to 2 parts by weight, (B-2) tryptophan 0 to 0.2 parts by weight, (B-3) asparagine 0 to 2 parts by weight, preferably, (A-2) 0.5 to 1.3 parts by weight, (A-3) 0.5 to 1.3 parts by weight, (A-4) 0.7 to 1.3 parts by weight, (A-5) 0.5 to 1.3 parts by weight, (B-1) 0 to 1.5 parts by weight, (B-2) 0.05 to 0.15 parts by weight, (B-3) 0.5 to 1.5 parts by weight, more preferably, (A-2) 0.5 to 1.1 part by weight, (A-3) 0.5 to 1.1 parts by weight, (A-4) 0.9 to 1.1 parts by weight, (A-5) 0.5 to 1.1 parts by weight, (B-1) 0.1 to 1.2 parts by weight, (B-2) 0.08 to 0.12 parts by weight, (B-3) 0.8 to 1.2 parts by weight, each per 1 part by weight of (A-1) tyrosine when converted to L form and free form.

The weight (%) of each amino acid in the composition of the present invention is generally (A-1) tyrosine 12 to 28 wt %, (A-2) serine 12 to 28 wt %, (A-3) alanine 12 to 28 wt %, (A-4) aspartic acid 12 to 28 wt % and (A-5) glutamic acid 12 to 30 wt %, preferably, (A-1) 14 to 25 wt %, (A-2) 14 to 25 wt %, (A-3) 14 to 25 wt %, (A-4) 14 to 25% and (A-5) 15 to 30 wt %, more preferably, (A-1) 14 to 22 wt %, (A-2) 14 to 22 wt %, (A-3) 14 to 22 wt %, (A-4) 18 to 22 wt % and (A-5) 18 to 30 wt %, each relative to the total amount of amino acids recited in (A) when converted to L form and free form.

The weight (%) of each amino acid in the composition of the present invention is generally (A-1) tyrosine 8 to 28 wt %, (A-2) serine 8 to 24 wt %, (A-3) alanine 8 to 24 wt %, (A-4) aspartic acid 8 to 28 wt % and (A-5) glutamic acid 8 to 24 wt %, and (B-1) hydroxyproline 0 to 32 wt %, (B-2) tryptophan 0 to 3.2 wt % and (B-3) asparagine 0 to 32 wt %, preferably, (A-1) 11 to 28 wt %, (A-2) 11 to 21 wt %, (A-3) 11 to 21 wt %, (A-4) 11% to 28% and (A-5) 11 to 21 wt %, and (B-1) 0 to 24 wt %, (B-2) 0.8 to 3 wt % and (B-3) 8 to 24 wt %, more preferably, (A-1) 14 to 28 wt %, (A-2) 11 to 18 wt %, (A-3) 11 to 18 wt %, (A-4) 14 to 28 wt % and (A-5) 11 to 18 wt %, and (B-1) 2.4 to 20 wt %, (B-2) 1.2 to 3 wt % and (B-3) 12 to 24 wt %, each relative to the total amount of amino acids recited in (A) and (B) when converted to L form and free form.

The amino acid in the present invention means a free amino acid, and does not include constituent amino acid in protein or peptide. In the present specification, the content of each amino acid is the content of amino acid in an L form. When the amino acid is contained in a salt form, the content is shown by the content converted to that of a free form. The amino acid composition of the present invention may contain an amino acid in a D form. When an amino acid in a DL form (L form:D form=1:1) is contained, the content can be converted based on the content of amino acid in an L form.

While the dose (ingestion amount) of the composition of the present invention may vary depending on the age, sex, body weight, target disease, symptom, and dosage form, the dose of (A) or (A) and (B) is generally 6 mg to 180 g, preferably 30 mg to 90 g, more preferably 60 mg to 45 g, further preferably 300 mg to 9 g, particularly preferably 600 mg to 4.5 g, for an adult (e.g., body weight 60 kg), which is administered or ingested in one to several portions per day.

The dose (ingestion amount) of tyrosine is generally 1 mg to 100 g, preferably 10 mg to 50 g, more preferably 50 mg to 10 g, further preferably 50 mg to 1 g, for an adult per day.

The dose (ingestion amount) of serine is generally 1 mg to 100 g, preferably 10 mg to 50 g, more preferably 50 mg to 10 g, further preferably 50 mg to 1 g, for an adult per day.

The dose (ingestion amount) of alanine is generally 1 mg to 100 g, preferably 10 mg to 50 g, more preferably 50 mg to 10 g, further preferably 50 mg to 1 g, for an adult per day.

The dose (ingestion amount) of aspartic acid is generally 1 mg to 100 g, preferably 10 mg to 50 g, more preferably 50 mg to 10 g, further preferably 50 mg to 1 g, for an adult per day.

The dose (ingestion amount) of glutamic acid is generally 1 mg to 100 g, preferably 10 mg to 50 g, more preferably 50 mg to 10 g, further preferably 50 mg to 1 g, for an adult per day.

The dose (ingestion amount) of hydroxyproline is generally 1 mg to 100 g, preferably 10 mg to 50 g, more preferably 50 mg to 10 g, further preferably 50 mg to 1 g, for an adult per day.

The dose (ingestion amount) of tryptophan is generally 1 mg to 50 g, preferably 10 mg to 10 g, more preferably 50 mg to 1 g, further preferably 50 mg to 0.1 g, for an adult per day.

The dose (ingestion amount) of asparagine is generally 1 mg to 100 g, preferably 10 mg to 50 g, more preferably 50 mg to 10 g, further preferably 50 mg to 1 g, for an adult per day.

The above-mentioned dose for an adult per day can be changed as appropriate in consideration of the sex, age, condition of the body such as disease and the like.

The above-mentioned dose of the composition of the present invention can be administered all at once or in several portions. The dosing period is not particularly limited, and long-term administration is possible since the active ingredient is amino acid.

In the composition of the present invention, the proportion of amino acid(s) other than (A) contained in the composition is not more than 50 wt %, preferably not more than 40 wt %, more preferably not more than 30 wt %, further preferably substantially nil, and particularly preferably nil, in total relative to the total weight of the composition when converted to a free form. Substantially not containing amino acid(s) other than (A) means containing not more than 0.2 wt %, preferably not more than 0.1 wt %, more preferably not more than 0.05 wt %.

In the composition of the present invention, the proportion of amino acid(s) other than (A) and (B) contained in the composition is not more than 50 wt %, preferably not more than 40 wt %, more preferably not more than 30 wt %, further preferably substantially nil, and particularly preferably nil, in total relative to the total weight of the composition when converted to a free form. Substantially not containing amino acid(s) other than (A) and (B) means containing not more than 0.2 wt %, preferably not more than 0.1 wt %, more preferably not more than 0.05 wt %.

The composition of the present invention can further contain, besides the amino acid in the present invention, other nutrition components such as carbohydrate, lipid, protein, vitamin, mineral and the like.

The composition of the present invention can be formulated into various forms such as liquid form (e.g., solution, suspension, emulsion and the like); semi-solid form (e.g., gel, cream and the like); solid form (e.g., powder, granule, tablet, capsule and the like) and the like by adding, where necessary besides amino acids of (A) in the present invention, the amino acids of (B), other nutrition components, pharmaceutically acceptable additives and the like and according to a formulating means well known in the field of preparations, for example, the methods described in the Japanese Pharmacopoeia preparation, seventeenth Edition, General Rules [3] preparation, each article, which is incorporated herein by reference in its entirety, and the like.

The above-mentioned pharmaceutically acceptable additive can be appropriately selected according to the dosage form of the composition of the present invention. For example, an excipient, binder, disintegrant, lubricant, coating agent, base, solvent, solubilizing agents, solubilizer, emulsifier, dispersing agent, suspending agent, stabilizer, thickener, soothing agent, isotonicity agent, pH adjuster, antioxidant, antiseptic, preservative, corrigent, sweetening agent, flavor, colorant and the like can be mentioned.

Specifically, examples of the excipient include magnesium carbonate, saccharides (glucose, lactose, cornstarch etc.), sugar alcohol (sorbitol, mannitol etc.) and the like.

Examples of the binder include gelatin, pregelatinized starch, partly pregelatinized starch, cellulose and a derivative thereof (crystalline cellulose, hydroxypropylcellulose etc.) and the like.

Examples of the disintegrant include crospovidone, povidone, crystalline cellulose and the like.

Examples of the lubricant include talc, magnesium stearate and the like.

Examples of the coating agent include methacrylic acid•methyl methacrylate copolymer, methacrylic acid•ethyl acrylate copolymer, methyl methacrylate•butyl methacrylate•methacrylic acid dimethylaminoethyl copolymer, ethyl acrylate•methyl methacrylate•methacrylic acid trimethylammonium chloride ethyl copolymer and the like.

Examples of the base include animal and plant fats and oils (olive oil, cacao butter, beef tallow, sesame oil, hydrogenated oil, castor oil etc.), wax (Carnauba wax, beeswax etc.), polyethylene glycol and the like.

Examples of the solvent include purified water, water for injection, monovalent alcohol (ethanol etc.), polyhydric alcohol (glycerol etc.) and the like.

Examples of the solubilizing agents include propylene glycol, medium-chain triglyceride and the like.

Examples of the solubilizer, emulsifier, dispersing agent and suspending agent include surfactants such as sorbitan fatty acid ester, glycerol fatty acid ester, polyoxyethylene sorbitan fatty acid ester (polysorbate20, polysorbate80 etc.), polyoxyethylene hydrogenated castor oil, sucrose fatty acid ester and the like, and the like.

Examples of the stabilizer include adipic acid, β-cyclodextrin, ethylenediamine, sodium edetate and the like.

Examples of the thickener include water-soluble polymers (sodium polyacrylate, carboxyvinyl polymer etc.), polysaccharides (sodium alginate, xanthan gum, tragacanth etc.) and the like.

Examples of the soothing agent include ethyl aminobenzoate, chlorobutanol, propylene glycol, benzyl alcohol and the like.

Examples of the isotonicity agent include potassium chloride, sodium chloride, sorbitol, saline and the like.

Examples of the pH adjuster include hydrochloric acid, sulfuric acid, acetic acid, citric acid, lactic acid, sodium hydroxide, potassium hydroxide and the like.

Examples of the antioxidant include dibutylhydroxytoluene (BHT), butylhydroxyanisole (BHA), dl-α-tocopherol, erythorbic acid and the like.

Examples of the antiseptic and preservative include paraben (methylparaben etc.), benzyl alcohol, sodium dehydroacetate, sorbic acid and the like.

Examples of the corrigent include ascorbic acid, erythritol, 14-sodium glutamate and the like.

Examples of the sweetening agent include aspartame, licorice extract, saccharin and the like.

Examples of the flavor include l-menthol, d-camphor, vanillin and the like.

Examples of the colorant include tar pigment (Food Color Red No. 2, Food Color Blue No. 1, Food Color yellow No. 4 etc.), inorganic pigment (red ferric oxide, yellow iron oxide, black iron oxide etc.), natural dye (turmeric extract, β-carotene, copper chlorophyllin sodium etc.) and the like.

In the present invention, one or more kinds of the above-mentioned additives can be used.

From the aspect of functionality, the total content of (A) in the composition of the present invention is generally 10 wt % to 100 wt %, preferably 50 wt % to 100 wt %, more preferably 60 wt % to 100 wt %, further preferably 70 wt % to 100 wt %, particularly preferably 80 wt % to 100 wt %, relative to the total amount of the composition.

From the aspect of functionality, the total content of (A) and (B) in the composition of the present invention is generally 10 wt % to 100 wt %, preferably 50 wt % to 100 wt %, more preferably 60 wt % to 100 wt %, further preferably 70 wt % to 100 wt %, particularly preferably 80 wt % to 100 wt %, relative to the total amount of the composition.

The composition of the present invention can be in the form of a package of a unit ingestion amount for one time or one meal, "unit package form". In such embodiment, the amount to be ingested once or per meal is determined in advance and packaged. The container or package used for the unit package form may be appropriately selected according to the form of the composition of the present invention and the like. Examples thereof include paper container or bag, plastic container or bag, pouch, aluminum can, steel can, bottle, plastic bottle, PTP (press through pack) packaging sheet and the like. In the case of drink, jelly, yogurt, gum, cookie or the like, for example, an amount to be ingested at one time is packaged in a container such as bag, pouch, bottle, box or the like. In the case of granule, powder, slurry or the like, for example, an amount to be ingested at one time is individually packaged in a pouch, bag or the like. Particularly, when the composition is a health food, food with functional claims, food with nutrient function claims, food for specified health uses and the like, for example, a form wherein the composition of the present invention is packed in a unit amount to be ingested once or per meal, a form wherein the composition of the present invention is suspended or dissolved to give a drink or a jelly, which is packaged in a pouch etc. for a single consumption or ingestion and the like can be mentioned.

The above-mentioned one time or one meal unit ingestion amount may contain (A) in a total amount of 6 mg to 180 g, preferably 30 mg to 90 g, more preferably 60 mg to 45 g.

The above-mentioned one time or one meal unit ingestion amount may contain (A) and (B) in a total amount of 6 mg to 180 g, preferably 30 mg to 90 g, more preferably 60 mg to 45 g.

In this way, ingestion of one time or one meal unit ingestion amount enables convenient ingestion of the necessary amount of amino acid.

Another embodiment of the present invention is a kit containing a measuring container and a composition containing 5 to 8 amino acids from tyrosine, serine, alanine, aspartic acid, glutamic acid, hydroxyproline, tryptophan and asparagine as active ingredients.

The measuring container is not particularly limited as long as it is a container for measuring the amount of single ingestion of the above-mentioned amino acids and, for example, a measuring cup, a measuring spoon and the like can be mentioned. The amount of single ingestion is the same as the above-mentioned amount for one time or one meal unit ingestion. The amount that can be measured by a measuring container can be determined according to the container such as a level amount, a heaping amount and the like. The measuring container may have a scale showing the amount of single use and the like.

The form of the composition of the present invention may be liquid (drinks and the like), jelly (jelly, gel, jelly drinks and the like), milky (milk, milk beverage, yogurt and the like), solid (gum, powdered, granular, sheet, capsule, tablet, candy bar, cookies and the like), and the like.

The composition of the present invention can be applied to mammals (e.g., human, monkey, mouse, rat, guinea pig, hamster, rabbit, cat, dog, bovine, horse, donkey, swine, sheep etc.), birds (e.g., duck, chicken, goose, turkey etc.) and the like.

When the composition of the present invention is applied to an application target animal other than human (hereinafter to be also simply referred to as "target animal"), the ingestion amount or dose of the composition of the present invention can be appropriately set according to the kind, sex, body weight and the like of the target animal.

The composition of the present invention can be provided as it is or a pharmaceutical product further containing the above-mentioned pharmaceutically acceptable additives (hereinafter to be also referred to as "the pharmaceutical product of the present invention" in the present specification).

The pharmaceutical product of the present invention can have a dosage form of oral preparation such as tablet, coating tablet, chewable tablet, pill, (micro)capsule, granule, fine granule, powder, elixir, lemonade, syrup, suspension, emulsion, oral jelly and the like, injection such as solution, suspension, emulsion and the like, solid injection to be used by dissolving or suspending when in use, injectable preparation such as transfusion, sustainable injection and the like, tube feeding liquid and the like.

The pharmaceutical product of the present invention can be preferably administered to a wide range of subjects feeling tired such as patients with brain dysfunction, particularly elderly people and middle-aged people and the like, elderly people and middle-aged people and the like who may exhibit the aforementioned disorder and the like, and elderly people and middle-aged people and the like with brain dysfunction.

The pharmaceutical product of the present invention is administered to the above-mentioned application subject such that the total amount of the amino acids in the present invention (total amount in terms of free form) would be the above-mentioned ingestion amount per day.

Furthermore, the composition of the present invention can be ingested by adding to various foods. The food to which the composition of the present invention is added is not particularly limited, and may be any as long as it is a food in the form generally served for meals and dessert. For example, the composition of the present invention may be added to drinks (e.g., beverage etc.), and a suitable flavor is added when desired, whereby a drink can be provided.

More specifically, the composition of the present invention can be added to, for example, beverage water such as fruit juice drinks, sport drinks and the like; milk product such as cow milk, yogurt and the like; confectionery such as jelly, chocolate, candy, biscuit and the like, and the like.

The composition of the present invention is preferably added to the above-mentioned various foods in amounts to be ingested per day such that the total amount of the amino acids in the present invention (total amount in terms of L form and free form) would be the above-mentioned ingestion amount per day.

The composition of the present invention can be provided as it is or as a food by adding general food additives where necessary by a general food production technique (hereinafter to be also referred to as "food of the present invention" in the present specification).

The food of the present invention can be formulated into various forms such as liquid, suspension, milk, gel, cream, powder, granule, sheet, capsule, tablet and the like.

Furthermore, the food of the present invention can be provided in various forms of foods containing the composition of the present invention and various food starting materials and, where necessary, general food additives by a general food production technique. Examples thereof include beverage water (fruit juice drinks, sport drinks, coffee drinks, tea drinks etc.), milk product (*lactobacillus* drinks, fermentation milk, butter, cheese, yogurt, processed milk, defatted milk etc.), meat product (ham, sausage, hamburger steak etc.), processed seafood paste product (fish cake, tube-shaped fish sausage, satumaage etc.), egg product (Japanese-style rolled omelette, egg tofu etc.), confectionery (cookie, jelly, chewing gum, candy, snack confectionery, frozen dessert etc.), bread, noodles, pickles, dried fish, boiled fish, soup, seasoning and the like. It may also be bottled food, canned food or retort pouch food.

Examples of the above-mentioned food additive include agents for production (kansui, binding agent etc.), thickening stabilizer (xanthan gum, sodium carboxymethylcellulose etc.), gelling agent (gelatin, agar, carrageenan etc.), gum base (vinyl acetate resin, jelutong, chicle etc.), emulsifier (glycerol fatty acid ester, sucrose fatty acid ester, saponin, lecithin etc.), preservative (benzoic acid, sodium benzoate, sorbic acid, potassium sorbate, ε-polylysine etc.), antioxidant (ascorbic acid, erythorbic acid, catechin etc.), gloss agent (shellac, paraffin wax, beeswax etc.), fungicide (thiabendazole, fludioxonil etc.), leavening agent (sodium hydrogen carbonate, glucono δ-lactone, alum etc.), sweetener (aspartame, acesulfame potassium, licorice extract etc.), bittering agent (caffeine, naringin, worm wood extract etc.), acidulant (citric acid, tartaric acid, lactic acid etc.), seasoning (L-sodium glutamate, disodium 5'-inosinate etc.), colorant (annatto dye, turmeric dye, *gardenia* dye etc.), flavor (synthetic flavor such as ethyl acetoacetate, anisaldehyde and the like, natural flavor such as orange, lavender and the like) and the like.

In the present invention, one or more kinds of the above-mentioned food additive can be used.

The food of the present invention can be preferably ingested by a wide range of subjects such as elderly people and middle-aged people and the like with symptoms of brain dysfunction, elderly people and middle-aged people and the like who may exhibit the aforementioned symptoms, and further for prevention of brain dysfunction or recovery or suppression of fatigue.

Therefore, the food of the present invention can also be provided as food with health claims such as a food for specified health uses, food with nutrient function claims, food with functional claims and the like, food for special dietary uses such as food for sick people, food for the elderly and the like, health supplement and the like for improvement of brain function or recovery or suppression of fatigue.

The food of the present invention is preferably given to the above-mentioned application subject such that the total amount of the amino acids in the present invention (total amount in terms of L form and free form) would be the above-mentioned ingestion amount per day.

Other features of the invention will become apparent in the course of the following descriptions of exemplary embodiments which are given for illustration of the invention and are not intended to be limiting thereof.

EXAMPLES

In the present specification, unless otherwise specified, % means wt %.

Example 1

Short Term Memory Evaluation and Measurement of Hippocampus Monoamine Level in Mental Stress Model (1-1) Production of Mental Stress Model A water floor stress model (exhaustion model) widely used as a chronic fatigue syndrome model or a gastric ulcer model was used. 10-week-old male C57 BL/6J mice (22 to 28 g) were bred for two days in a cage covered with 0.5 cm water with free access to food and water intake. As the feed, AIN-93G composition diet was used.

(1-2) During this period, amino acid BAA solution (1.2 g/kg) containing hydroxyproline, asparagine, serine, alanine, tyrosine, tryptophan, aspartic acid and glutamic acid was orally administered by sonde to the test group, and water was orally administered by sonde to the normal group and control group at a dose of 20 ml/kg, each twice in the morning and evening per day. The composition ratio of BAA is shown in Table 1 and the group constitution is shown in Table 2. The values of amino acids in Table 1 are those after conversion to L form and free form.

(1-3) In the morning of day 3, the amino acid BAA solution (1.2 g/kg) or water was orally administered by sonde at a dose of 20 ml/kg, the below-mentioned Y-maze was performed one hour later and cognitive function was evaluated. Thereafter, the brain was collected under anesthesia. In addition, blood, liver and thalamus were collected.

TABLE 1

| | weight ratio (%) |
|---|---|
| Hypro | 14.1 |
| Trp | 1.3 |
| Asn | 14.1 |
| Ser | 14.1 |
| Ala | 14.1 |
| Asp | 14.1 |
| Glu | 14.1 |
| Tyr | 14.1 |

TABLE 2

| group constitution | n |
|---|---|
| Normal normal group + water | 8 |
| Control stress load + water | 8 |
| BAA stress load + BAA 1.2 g/kg p.o. | 8 |

(1) Y-Maze Test (Y-Maze Task)

In the Y-maze test, a Y-shaped maze apparatus formed by connecting three arms (size: length 40 cm×width 10 cm×height 13 cm) was used. In the test, a mouse was placed on the tip of any arm and allowed to freely explore in the maze for 8 min. In this occasion, entry of the hindlimb of the mouse into the arm was regarded as the invasion into the arm, and the total number of times the mouse moved between arms was taken as the total number of invasion. Among these, the total number of times when three different arms were selected in succession was taken as the number of spontaneous alternation behaviors. The number of spontaneous alternation behaviors was divided by a number obtained by subtracting 2 from the total number of invasion and the resulting number was multiplied by 100. The obtained value was taken as the spontaneous alternation behavior change rate (Alternation) and used as an index of spontaneous alternation behavior. As a significant difference test, Holm-Sidak's multiple comparisons test was used (*: $P<0.05$).

Based on these tests, the amount of spontaneous behavior and spacial working memory (working memory) of the mouse were evaluated.

Results

The results are shown in FIG. 1. A higher Y-maze (alternation) value suggests high cognitive function. BAA significantly improved short term memory of the mouse.

(2) Blood GOT, GPT Measurement

To measure liver leakage enzyme in the blood, Fuji DRI-CHEM system was used to measure glutamic oxaloacetic transaminase (GOT) and glutamic pyruvic transaminase (GPT).

GOT and GPT are known to leak out from the liver into blood during liver fatigue, and are one of the indices of liver fatigue.

Results

Figure 2:
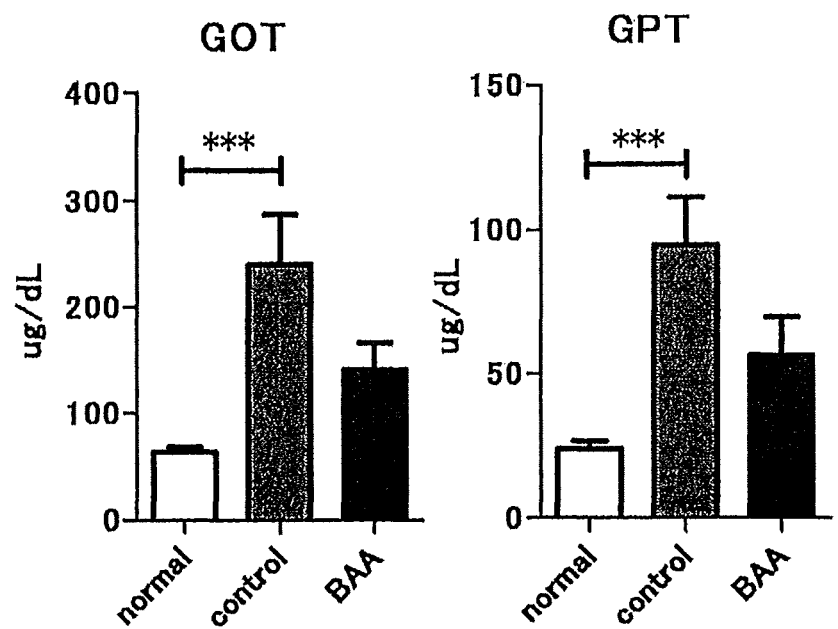
FIG. 2 is a graph showing that a BAA composition suppresses liver fatigue in a mental stress model. GOT: glutamic oxaloacetic transaminase and GPT: glutamic pyruvic transaminase are each an enzyme that leaks out from the liver into blood during liver fatigue and is one of the indices of liver fatigue. Normal: a group generally reared with oral administration of water. Control: a group reared in a cage with water with oral administration of water. BAA: a group reared in a cage with water with oral administration of amino acid composition BAA. $P<0.001$ in two groups connected by ***.

The results are shown in FIG. 2. The blood GOT, GPT significantly increased in the mental stress model and addition of a BAA composition suppressed GOT and GPT.

(3) Analysis of ATF3 Expression in Liver and Thalamus mRNA in the liver and thalamus was extracted by a conventional method and ATF3 gene expression was analyzed. As the primer, ATF3-F and ATF3-R were used.

```
ATF3-F
                                            (SEQ ID NO: 1)
GAGGATTTTGCTAACCTGACACC

ATF3-R
                                            (SEQ ID NO: 2)
TTGACGGTAACTGACTCCAGC
```

ATF3 is a transcription factor identified as a fatigue factor and is known to express in each tissue during fatigue.

Results

Figure 3:
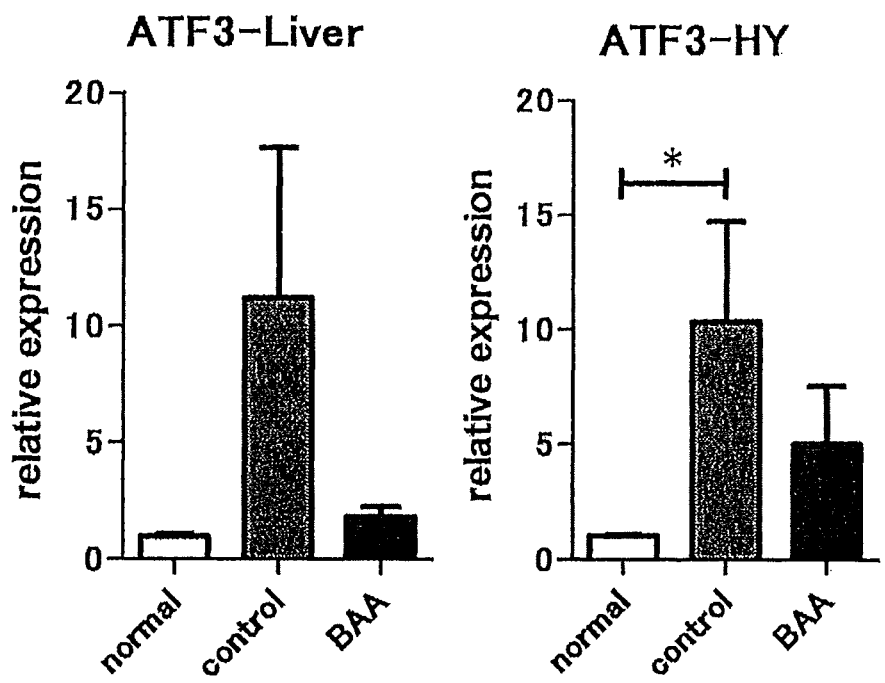
FIG. 3 is a graph showing that a BAA composition suppresses liver and thalamus fatigue in a mental stress model. ATF3: a transcription factor identified as a fatigue factor and is known to express in each tissue during fatigue. Normal: a group generally reared with oral administration of water. Control: a group reared in a cage with water with oral administration of water. BAA: a group reared in a cage with water with oral administration of amino acid composition BAA. Liver: liver, HY: thalamus. $P<0.05$ in two groups connected by *.

The results are shown in FIG. 3. In the mental fatigue model, ATF3 gene expression in the liver and thalamus increased, and addition of the BAA composition suppressed ATF3 gene expression.

(4) Hippocampus Monoamine Value Measurement

Hippocampus was homogenized and extracted and the resulting solution was analyzed for peak by HPLC, and norepinephrine (NE), dopamine (DA) and serotonin (5-HT) values were analyzed.

Results

Figure 4:
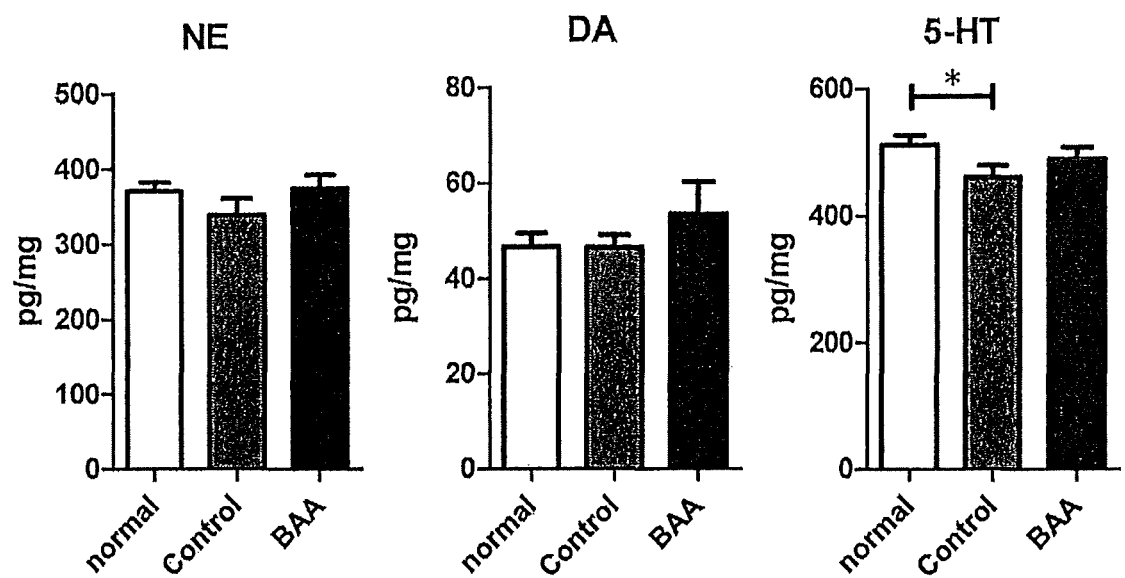
FIG. 4 is a graph showing a reducing effect of a BAA composition on a decrease in the hippocampus monoamine amount in a mental stress model. Normal: a group generally reared with oral administration of water. Control: a group reared in a cage with water with oral administration of water. BAA: a group reared in a cage with water with oral administration of amino acid composition BAA. NE: norepinephrine, DA: dopamine, 5-HT: serotonin. $P<0.05$ in two groups connected by *.

The results are shown in FIG. 4. A higher monoamine value suggests possibility of high cognitive function.

The monoamine value of hippocampus increased by BAA administration when compared to the control group.

Example 2

Cognitive Function Evaluation in Exercise Fatigue Model
(1) Production of Exercise Fatigue Model
(1-1) Male 10-week-old C57 BL/6J mice (22 to 28 g) were made to run until exhaustion in a treadmill to construct an exercise fatigue model. The mice were made to run in the treadmill at a speed of 20 m/min for 0 to 30 min after the start, 22 m/min from 30 to 60 min after the start, and 24 m/min after 60 min until exhaustion. The mouse that stopped running was turned over and the state of exhaustion was judged when the mouse could not get up by itself.
(1-2) Immediately after running, any of amino acid solutions BAA and BAA1-4 prepared at the composition ratios shown in Table 3 or water was orally administered by sonde at a dose of 20 ml/kg, and NORT was evaluated one hour later. The composition ratios of BAA and BAA1-4 are shown in Table 3, and the group constitution is shown in Table 4. The values of amino acids in Table 3 are those after conversion to L form and free form (*: DL-Ala was used for alanine alone in BAA4, 14.35% when converted to L-Ala).

TABLE 3

| | weight ratio (%) | | | | |
|---|---|---|---|---|---|
| | BAA | BAA1 | BAA2 | BAA3 | BAA4 |
| Hypro | 3.0 | | 2.7 | | |
| Trp | 1.6 | 2.7 | | | |
| Asn | 15.9 | | | 22.2 | |
| Ser | 15.9 | 13.9 | 13.9 | 11.1 | 14.2 |
| Ala | 15.9 | 13.9 | 13.9 | 11.1 | 28.7* |
| Asp | 15.9 | 27.8 | 27.8 | 22.2 | 14.2 |
| Glu | 15.9 | 13.9 | 13.9 | 11.2 | 28.7 |
| Tyr | 15.9 | 27.8 | 27.8 | 22.2 | 14.2 |

TABLE 4

| group constitution | n |
|---|---|
| Sedentary nonexercise group + water | 8 |
| Exhaust exercise fatigue group + water | 12 |
| BAA exercise fatigue + BAA 1.2 g/kg p.o. | 11 |
| BAA1 exercise fatigue + BAA1 0.69 g/kg p.o. | 9 |
| BAA2 exercise fatigue + BAA2 0.69 g/kg p.o. | 10 |
| BAA3 exercise fatigue + BAA3 0.86 g/kg p.o. | 12 |
| BAA4 exercise fatigue + BAA4 0.67 g/kg p.o. | 9 |

(2) NORT (Novel Object Recognition Test) Evaluation

When mice enter a new environment, they start explore behavior and become acclimated to the environment with the lapse of time, and their behavior quantity decreases. Similarly for object recognition, the explore behavior is found when there is a new object, and the behavior quantity decreases as the novelty decreases. NORT is a method of measuring learning and memory by the use of this explore behavior for an object as an index.

For NORT evaluation, an open-field apparatus (40 cm×40 cm×40 cm) was used. On day 1, a mouse was allowed to act freely for 10 min in the absence of an object to be the explore target, and was acclimated to the environment. On day 2, training was conducted (PRE) and the test was conducted on day 3 (TEST). In PRE, the same two objects A, B were placed diagonally in the field and the mouse was allowed to explore freely for 10 min. In TEST, of the target objects used in PRE, object A with a shorter explore time was replaced with another target object C, and the mouse was allowed to explore freely for 10 min. The state in which the nose of the mouse is within 1 cm from the object and the mouse sniffs the object or its body touches the object is defined as the explore behavior and the explore time of each object was measured. The recognition index (%) of the object was calculated as follows.

PRE: explore time of object A/explore time of object A+explore time of object B
TEST: explore time of object C/explore time of object B+explore time of object C By comparison of the recognition index between PRE and TEST, when the object explored once is remembered, the recognition index of TEST showing the explore ratio of a new object increases, and when it is not remembered, the index does not change compared with PRE.

Mouse with a total explore time of not more than 10 seconds was excluded from the test.

Figure 5:
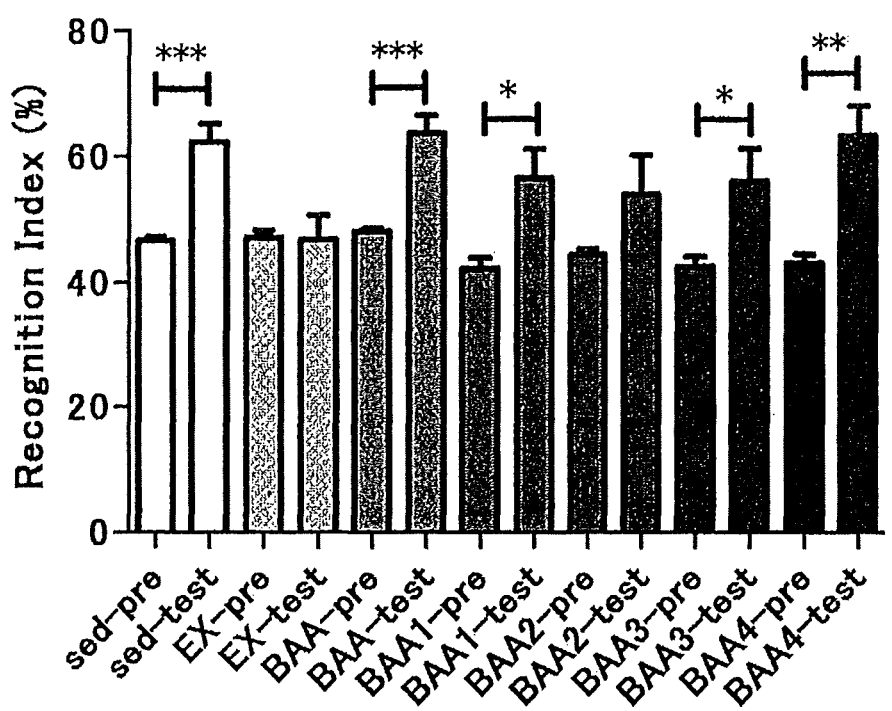
FIG. 5 is a graph showing an improving effect of a BAA composition and a BAA1-4 composition on cognitive decline in an exercise fatigue model. Sed: a group without exercise. EX: a group with exercise and oral administration of water immediately after completion of exercise. BAA, BAA1-4: a group with exercise and oral administration of BAA or BAA1-4 immediately after completion of exercise. $P<0.05$ in two groups in which Pre and test are connected by *, $P<0.01$ in two groups in which Pre and test are connected by , and $P<0.001$ in two groups in which Pre and test are connected by *.

As a significant difference test of PRE and TEST, paired t-test was used (*: $P<0.05$, : $P<0.01$, *: $P<0.001$).
Results The results are shown in FIG. 5. Sed shows a group administered with water and free of exercise fatigue. EX shows a group with exercise fatigue and administered with water or BAA. When the NORT (RI) value during the TEST is significantly higher than the PRE value, the cognitive function is high. The group free of exercise fatigue showed high cognitive function and the group with exercise fatigue showed cognitive decline. In contrast, the BAA administration group showed improvement in cognitive decline during exercise fatigue. Similarly in BAA1-4, improvement in cognitive decline during exercise fatigue was also found.

Figure 6:
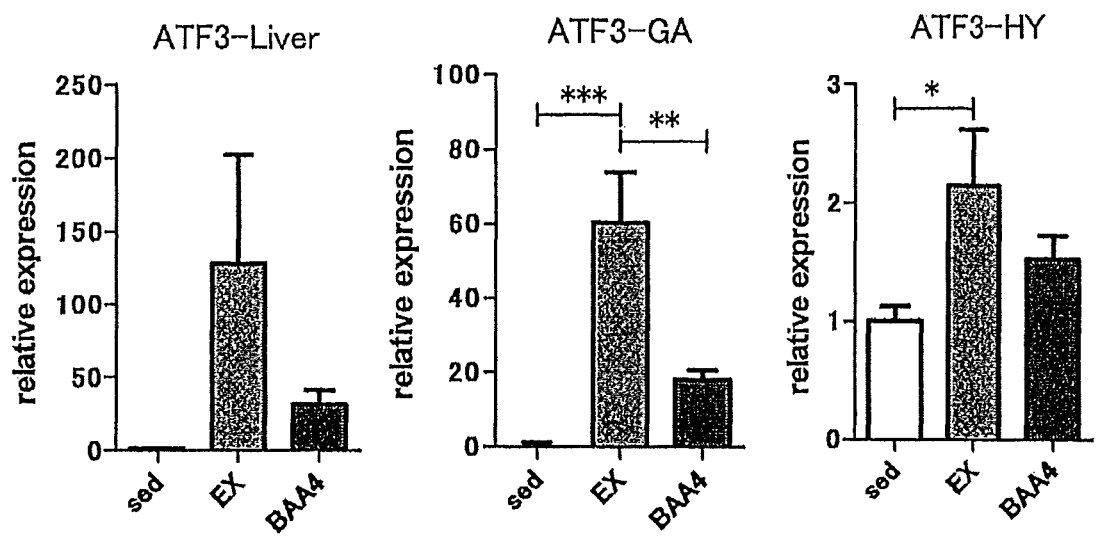
FIG. 6 is a graph showing that BAA4 suppresses fatigue in the liver, gastrocnemial muscle and thalamus in an exercise fatigue model. ATF3: a transcription factor identified as a fatigue factor and is known to express in each tissue during fatigue. Sed: a group without exercise. EX: a group with exercise and oral administration of water immediately after completion of exercise. BAA4: a group with exercise and oral administration of BAA4 immediately after completion of exercise. $P<0.05$ in two groups in which Pre and test are connected by *, $P<0.01$ in two groups in which Pre and test are connected by , and $P<0.001$ in two groups in which Pre and test are connected by *.

(3) Analysis of ATF3 Expression in Liver, Gastrocnemial Muscle and Thalamus mRNA in the liver, gastrocnemial muscle and thalamus was extracted by a conventional method and ATF3 gene expression was analyzed. As the primer, ATF3-F and ATF3-R were used.
Results The results are shown in FIG. 6. In the exercise fatigue model, ATF3 gene expression in the liver, gastrocnemial muscle and thalamus increased, and addition of the BAA composition suppressed ATF3 gene expression.

(4) Analysis of Hepcidin (Hamp) Expression in Liver mRNA in the liver was extracted by a conventional method and Hamp gene expression was analyzed. As the primer, MA158770-F and MA158770-R were used.

```
MA158770-F
                                        (SEQ ID NO: 3)
GCCTGAGCAGCACCACCTAT

MA158770-R
                                        (SEQ ID NO: 4)
AGCATTTACAGCAGAAGATGCAGA
```

Figure 7:
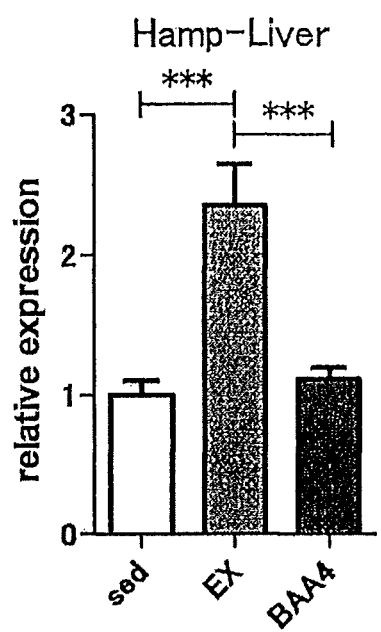
FIG. 7 is a graph showing that BAA4 suppresses liver fatigue in an exercise fatigue model. Hamp: a gene of hepcidin which is produced in the liver and controls iron metabolism, and is known to show increased expression during liver fatigue. Sed: a group without exercise. EX: a group with exercise and oral administration of water immediately after completion of exercise. BAA4: a group with exercise and oral administration of BAA4 immediately after completion of exercise. $P<0.001$ in two groups in which Pre and test are connected by ***.

Hamp is a gene of hepcidin that is produced in the liver and controls iron metabolism. It is known that the expression level thereof increases during liver fatigue.
Results The results are shown in FIG. 7. In the exercise fatigue model, Hamp gene expression in the liver increased, and addition of BAA4 suppressed Hamp gene expression.

INDUSTRIAL APPLICABILITY

The present invention can provide a composition effective for brain function improvement, fatigue recovery or fatigue suppression.

The invention claimed is:

1. A method for improving cognitive decline caused by mental or physical stress, comprising:
administering an effective amount of a composition which comprises (A) tyrosine, serine, alanine, aspartic acid and glutamic acid as active ingredients to a subject in need thereof,
wherein blending ratios in the composition are 0.5 to 1.5 parts by weight of serine, 0.5 to 1.5 parts by weight of alanine, 0.5 to 1.5 parts by weight of aspartic acid and 0.5 to 2.5 parts by weight of glutamic acid, per 1 part by weight of tyrosine, and
a total amount of amino acids other than (A) in the composition, when converted to a free form, is not more than 50 wt % relative to a weight of the composition.

2. The method according to claim 1, wherein said composition further comprises (B) at least one member selected from the group consisting of hydroxyproline, tryptophan and asparagine.

3. The method according to claim 1, wherein blending ratios in the composition are 0.7 to 1.3 parts by weight of serine, 0.7 to 1.3 parts by weight of alanine, 0.7 to 1.3 parts by weight of aspartic acid and 0.7 to 2.1 parts by weight of glutamic acid, per 1 part by weight of tyrosine.

4. The method according to claim 2, wherein blending ratios in the composition are 0 to 2 parts by weight of hydroxyproline, 0 to 0.2 parts by weight of tryptophan and 0 to 2 parts by weight of asparagine, per 1 part by weight of tyrosine.

5. The method according to claim 1, wherein said composition is in a unit package form per serving comprising 6 mg to 180 g in total of (A) in the unit for single ingestion.

6. The method according to claim 2, wherein said composition is in a unit package form per serving comprising 6 mg to 180 g in total of (A) and (B) in the unit for single ingestion.

7. A method for improving or accelerating recovery from fatigue in liver, muscle, or thalamus, comprising:
administering an effective amount of a composition which comprises (A) tyrosine, serine, alanine, aspartic acid and glutamic acid as active ingredients to a subject in need thereof,
wherein blending ratios in the composition are 0.5 to 1.5 parts by weight of serine, 0.5 to 1.5 parts by weight of alanine, 0.5 to 1.5 parts by weight of aspartic acid and 0.5 to 2.5 parts by weight of glutamic acid, per 1 part by weight of tyrosine, and a total amount of amino acids other than (A) in the composition, when converted to a free form, is not more than 50 wt % relative to a weight of the composition.

8. The method according to claim 7, wherein said composition further comprises (B) at least one member selected from the group consisting of hydroxyproline, tryptophan and asparagine.

9. The method according to claim 1, wherein said total amount of amino acids other than (A) in the composition, when converted to a free form, is not more than 40 wt % relative to the weight of the composition.

10. The method according to claim 1, wherein said total amount of amino acids other than (A) in the composition, when converted to a free form, is not more than 30 wt % relative to the weight of the composition.

11. The method according to claim 1, wherein said total amount of amino acids other than (A) in the composition, when converted to a free form, is substantially nil.

12. The method according to claim 2, wherein a total amount of amino acids other than (A) and (B) in the composition, when converted to a free form, is not more than 50 wt % relative to a weight of the composition.

13. The method according to claim 1, wherein a total amount of amino acids other than tyrosine, serine, alanine, aspartic acid, glutamic acid, hydroxyproline, tryptophan and asparagine in the composition, when converted to a free form, is not more than 0.2 wt % relative to the weight of the composition.

* * * * *